US010952843B2

(12) United States Patent
Matheny

(10) Patent No.: US 10,952,843 B2
(45) Date of Patent: *Mar. 23, 2021

(54) PROSTHETIC TISSUE VALVES

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 336 days.

This patent is subject to a terminal disclaimer.

(21) Appl. No.: 16/129,968

(22) Filed: Sep. 13, 2018

(65) Prior Publication Data

US 2019/0008634 A1    Jan. 10, 2019

Related U.S. Application Data

(63) Continuation-in-part of application No. 15/206,833, filed on Jul. 11, 2016, now Pat. No. 10,188,510, and
(Continued)

(51) Int. Cl.
*A61F 2/24* (2006.01)
*A61L 27/36* (2006.01)
(Continued)

(52) U.S. Cl.
CPC ........ *A61F 2/2412* (2013.01); *A61L 27/3604* (2013.01); *A61L 27/3629* (2013.01); *A61L 27/3633* (2013.01); *A61L 27/3826* (2013.01); *A61L 27/3834* (2013.01); *A61L 27/50* (2013.01); *A61F 2/246* (2013.01); *A61F 2/2409* (2013.01); *A61F 2/2457* (2013.01); *A61F 2210/0014* (2013.01); *A61F 2220/0075* (2013.01); *A61F 2230/0067* (2013.01); *A61L 27/367* (2013.01); *A61L 27/3873* (2013.01); *A61L 2300/104* (2013.01); *A61L 2300/404* (2013.01); *A61L 2300/406* (2013.01); *A61L 2300/41* (2013.01); *A61L 2300/414* (2013.01); *A61L 2300/416* (2013.01);
(Continued)

(58) Field of Classification Search
CPC ..... A61F 2/2454; A61F 2/2457; A61F 2/2469
See application file for complete search history.

(56) References Cited

U.S. PATENT DOCUMENTS 10,188,510 B2 * 1/2019 Matheny ............... A61F 2/2457
2007/0043431 A1 * 2/2007 Melsheimer .......... A61F 2/2475
623/1.24
(Continued)

FOREIGN PATENT DOCUMENTS

WO    WO-2016/050751 A1    4/2016

*Primary Examiner* — Megan Y Wolf
(74) *Attorney, Agent, or Firm* — Francis Law Group

(57) ABSTRACT

A prosthetic valve comprising a conical shaped ribbon structure comprising an extracellular matrix (ECM) composition. The ribbon structure comprises a plurality of elongated ribbon members that are positioned proximate each other in a joined relationship, wherein the ribbon members are positioned adjacent each other and form a plurality of fluid flow modulating regions that open when fluid flow through the valve exhibits a negative flow pressure and open when fluid flow through the valve exhibits a positive flow pressure.

5 Claims, 9 Drawing Sheets

Related U.S. Application Data a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
*A61L 27/38* (2006.01)
*A61L 27/50* (2006.01)

(52) U.S. Cl.
CPC ..... *A61L 2300/42* (2013.01); *A61L 2300/606* (2013.01); *A61L 2430/20* (2013.01)

(56) References Cited

U.S. PATENT DOCUMENTS

| | | | |
|---|---|---|---|
| 2014/0330369 A1* | 11/2014 | Matheny | A61F 2/24 623/2.14 |
| 2016/0317293 A1* | 11/2016 | Matheny | A61L 27/54 |
| 2017/0100512 A1* | 4/2017 | Matheny | A61F 2/2478 |

* cited by examiner

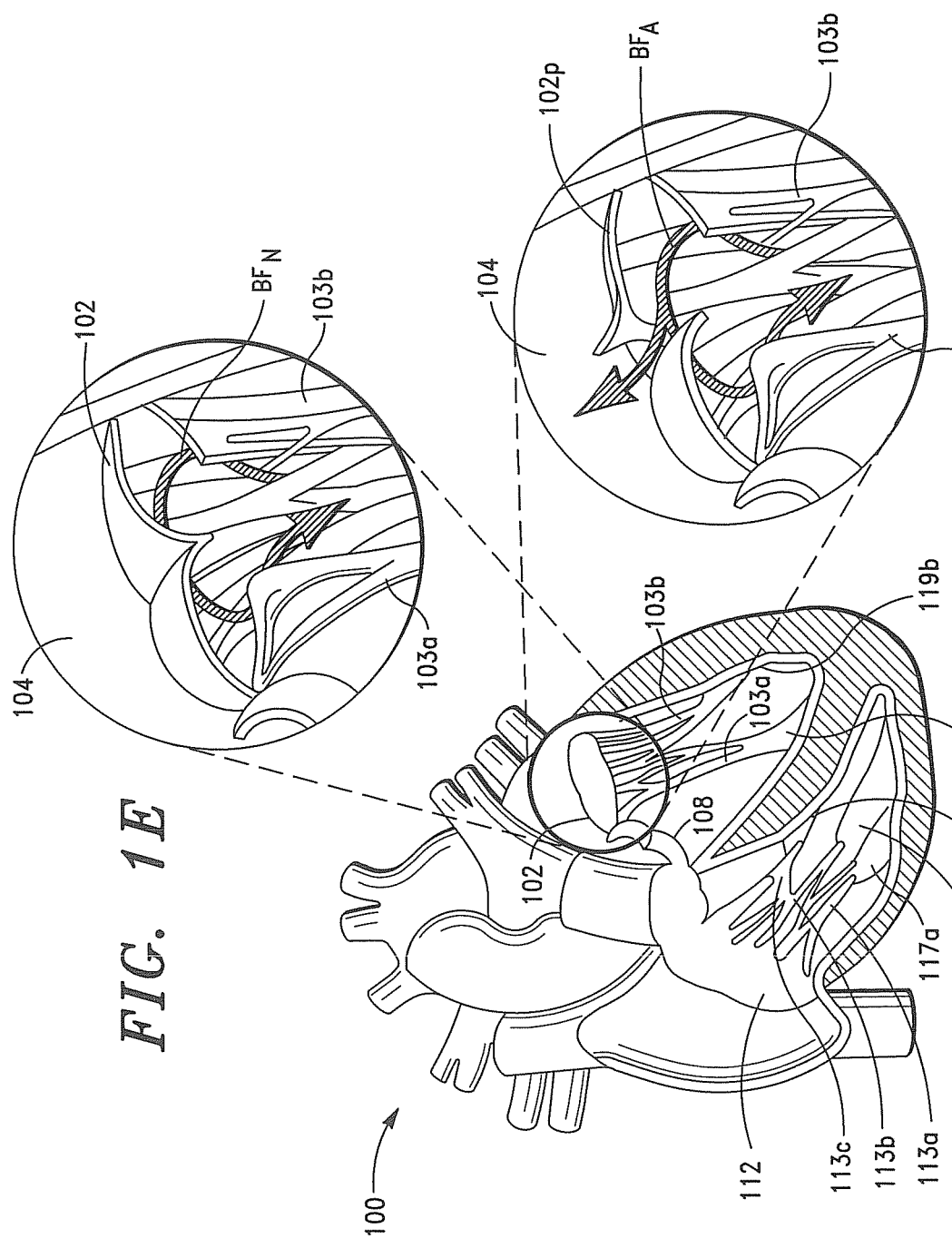

PROSTHETIC TISSUE VALVES

CROSS-REFERENCE TO RELATED APPLICATIONS

This application is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to prosthetic valves for replacing defective cardiovascular valves. More particularly, the present invention relates to prosthetic atrioventricular valves and methods for anchoring same to cardiovascular structures and/or tissue.

BACKGROUND OF THE INVENTION

As is well known in the art, the human heart has four valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIGS. 1C and 1D, there are also generally five papillary muscles in the heart 100; three in the right ventricle 116 and two in the left ventricle 106. The anterior, posterior and septal papillary muscles 117a, 117b, 117c of the right ventricle 116 each attach via chordae tendinae 113a, 113b, 113c to the tricuspid valve 112. The anterior and posterior papillary muscles 119a, 119b of the left ventricle 106 attach via chordae tendinae 103a, 103b to the mitral valve 102 (see also FIG. 1E).

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordeae or several disease states. Stenosis and insufficiency can also occur concomitantly in the same valve or in different valves.

Both of the noted valve abnormalities can adversely affect organ function and result in heart failure. By way of example, referring first to FIG. 1E, there is shown normal blood flow (denoted "$BF_N$") proximate the mitral valve 102 during closure. Referring now to FIG. 1F, there is shown abnormal blood flow (denoted "$BF_A$") or regurgitation caused by a prolapsed mitral valve 102p. As illustrated in FIG. 1F, the regurgitated blood "$BF_A$" flows back into the left atrium, which can, if severe, result in heart failure.

In addition to stenosis and insufficiency of a heart valve, surgical intervention may also be required for certain types of bacterial or fungal infections, wherein the valve may continue to function normally, but nevertheless harbors an overgrowth of bacteria (i.e. "vegetation") on the valve leaflets. The vegetation can, and in many instances will, flake off (i.e. "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize to the lungs. The noted embolization can, and in many instances will, result in lung dysfunction.

Treatment of the noted heart valve dysfunctions typically comprises reparation of the diseased heart valve with preservation of the patient's own valve or replacement of the valve with a mechanical or bioprosthetic valve, i.e. a prosthetic valve.

Various prosthetic heart valves have thus been developed for replacement of natural diseased or defective heart valves. Illustrative are the tubular prosthetic tissue valves disclosed in Applicant's U.S. Pat. Nos. 9,044,319, 8,709,076 and 8,790,397, and Co-Pending U.S. application Ser. Nos. 13/560,573, 13/804,683, 13/480,347 and 13/480,324. A further tubular prosthetic valve is disclosed in U.S. Pat. Nos. 8,257,434 and 7,998,196.

Heart valve replacement requires a great deal of skill and concentration to achieve a secure and reliable attachment of a prosthetic valve to a cardiovascular structure or tissue. Various surgical methods for implanting a prosthetic valve have thus been developed.

The most common surgical method that is employed to implant a prosthetic valve (mitral or tricuspid) comprises suturing a circular synthetic ring of a prosthetic valve to the annular tissue of the heart where a diseased valve has been removed.

A major problem associated with prosthetic valves is tissue valves with gluteraldehyde cross-linked leaflets will calcify and deteriorate over time.

Another problem is mechanical valves will require anticoagulation agents, such as Coumadin, which can cause side effects in high doses, such as uncontrolled bleeding.

Another problem is the valves do not remodel into normal tissue capable of regeneration and self-repair.

Another problem is many valves must be placed with open heart surgery while the patient is on a heart-lung machine.

There is thus a need to provide improved prosthetic tissue valves and methods for attaching same to cardiovascular structures and/or tissue that maintain or enhance the structural integrity of the valve when subjected to cardiac cycle induced stress.

It is therefore an object of the present invention to provide improved prosthetic tissue valves and methods for implanting same that overcome the drawbacks and disadvantages associated with conventional prosthetic atrioventricular valves.

It is another object of the present invention to provide improved prosthetic tissue valves and methods for attaching same to cardiovascular structures and/or tissue that maintain or enhance the structural integrity of the valve when subjected to cardiac cycle induced stress.

It is another object of the present invention to provide improved prosthetic tissue valves and methods for attaching same to cardiovascular structures and/or tissue that preserve the structural integrity of the cardiovascular structure(s) when attached thereto.

It is another object of the present invention to provide improved methods for securely attaching prosthetic tissue valves to cardiovascular structures and/or tissue.

It is another object of the present invention to provide prosthetic tissue valves having means for secure, reliable, and consistently highly effective attachment to cardiovascular structures and/or tissue.

It is another object of the present invention to provide extracellular matrix (ECM) prosthetic tissue valves that induce host tissue proliferation, bioremodeling and regeneration of new tissue and tissue structures with site-specific structural and functional properties.

It is another object of the present invention to provide ECM prosthetic tissue valves that induce adaptive regeneration.

It is another object of the present invention to provide ECM prosthetic tissue valves that are capable of administering a pharmacological agent to host tissue and, thereby produce a desired biological and/or therapeutic effect.

SUMMARY OF THE INVENTION

The present invention is directed to prosthetic tissue valves that can be readily employed to selectively replace diseased or defective heart valves, and methods for attaching (or anchoring) same to cardiovascular structures and/or tissue.

In some embodiments of the invention, the prosthetic tissue valves comprise continuous conical shaped structural members.

In some embodiments of the invention, the prosthetic tissue valves comprise continuous tubular sheet members.

In some embodiments of the invention, the prosthetic tissue valves comprise ribbon structures.

In some embodiments of the invention, the ribbon structures comprise a plurality of elongated ribbon members.

In a preferred embodiment of the invention, the edge regions of the ribbon members are positioned proximate each other and form a plurality of fluid flow modulating regions.

In a preferred embodiment, the distal ends of the ribbon members are in a joined relationship, wherein fluid flow through the joined distal ends of the ribbon members is restricted.

In some embodiments of the invention, each ribbon member is also joined to adjacent ribbon members by an integral coupling member.

In some embodiments of the invention, the proximal end of the prosthetic tissue valves includes an annular ring that is designed and configured to securely engage the prosthetic tissue valves to a valve annulus and, hence, cardiovascular tissue associated therewith.

In some embodiments of the invention, the distal end of the prosthetic tissue valves also comprise a structural ring.

According to the invention, the prosthetic tissue valves, annular ring and structural ring can comprise various biocompatible materials.

In some embodiments of the invention, the prosthetic tissue valves and/or annular ring and/or structural ring comprise an ECM composition comprising acellular ECM derived from mammalian tissue.

In a preferred embodiment of the invention, the mammalian tissue comprises small intestine submucosa (SIS), urinary bladder submucosa (UBS), stomach submucosa (SS), mesothelial tissue, gastrointestinal tissue, tissue surrounding growing bone, placental tissue, omentum tissue, cardiac tissue, kidney tissue, pancreas tissue or lung tissue, and combinations thereof.

In some embodiments of the invention, the ECM composition (and, hence, prosthetic tissue valves and/or annular ring and/or structural ring formed therefrom) further comprises at least one additional biologically active agent or composition, i.e. an agent that induces or modulates a physiological or biological process, or cellular activity, e.g., induces proliferation, and/or growth and/or regeneration of tissue.

In some embodiments of the invention, the biologically active agent comprises a growth factor, including, without limitation, transforming growth factor beta (TGF-β), fibroblast growth factor-2 (FGF-2), and vascular epithelial growth factor (VEGF).

In some embodiments of the invention, the biologically active agent comprises a growth factor, including, without limitation, human embryonic stem cells, myofibroblasts, mesenchymal stem cells, and hematopoietic stem cells.

In some embodiments of the invention, the biologically active agent comprises an exosome.

In some embodiments of the invention, the ECM composition (and, hence, prosthetic tissue valves and/or annular ring and/or structural ring formed therefrom) further comprises at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include, without limitation, antibiotics, anti-fibrotics, antiviral agents, analgesics, anti-inflammatories, anti-neoplastics, anti-spasmodics, and anti-coagulants and/or anti-thrombotic agents.

In some embodiments of the invention, the pharmacological agent comprises a statin, i.e. a HMG-CoA reductase inhibitor, such as cerivastatin.

In some embodiments of the invention, the pharmacological agent comprises an antibiotic, such as vancomycin and gentamicin.

In some embodiments of the invention, the pharmacological agent comprises an antimicrobial, such as silver particles and copper particles.

In some embodiments of the invention, the prosthetic tissue valves and/or annular ring and/or structural ring comprise a polymeric composition.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A-1D are schematic illustrations of a human heart;

FIG. 1E is an illustration of a normal mitral valve;

FIG. 1F is an illustration of a prolapsed mitral valve;

DETAILED DESCRIPTION OF THE PREFERRED EMBODIMENT

Figure 1A:
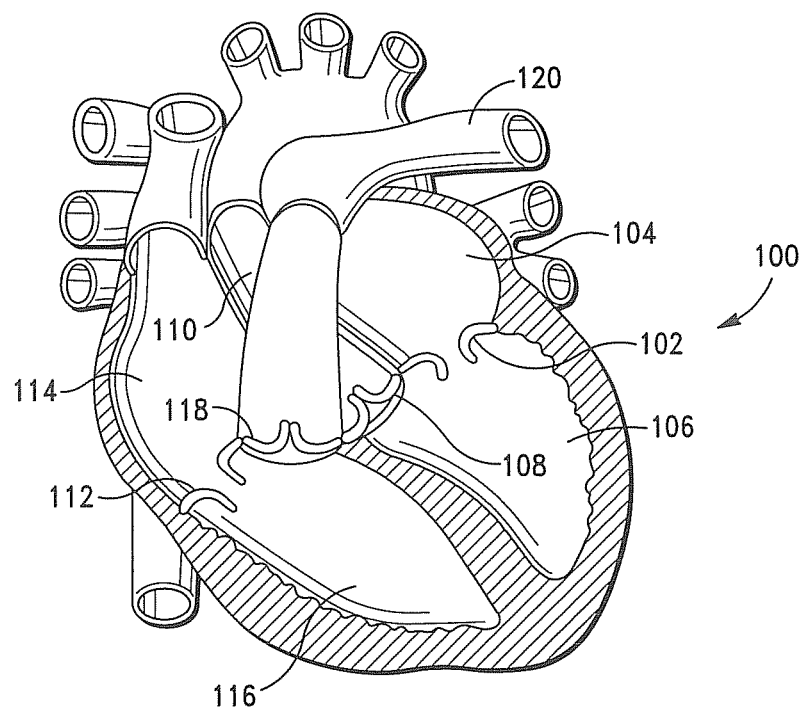
Figure 1B:
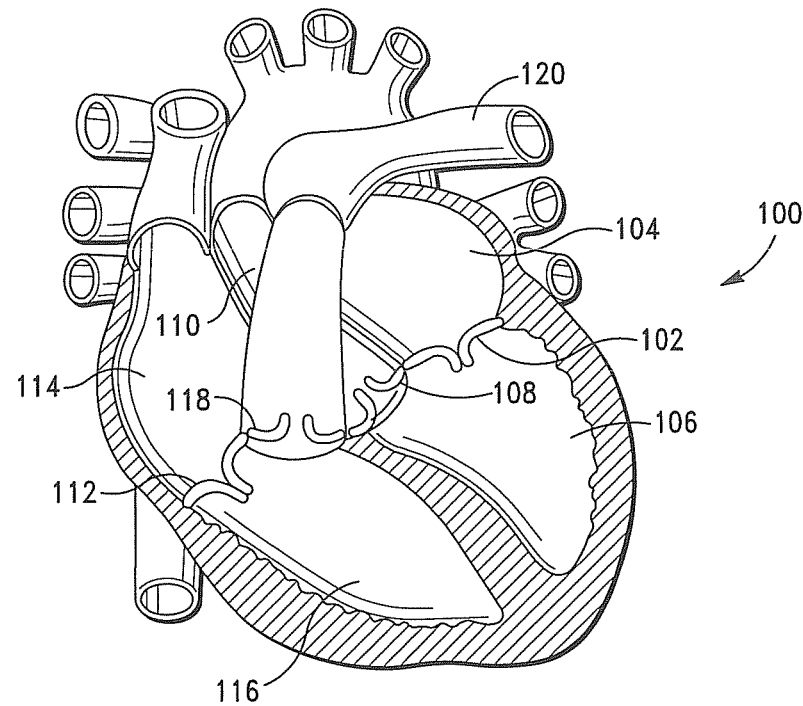
Figure 1C:
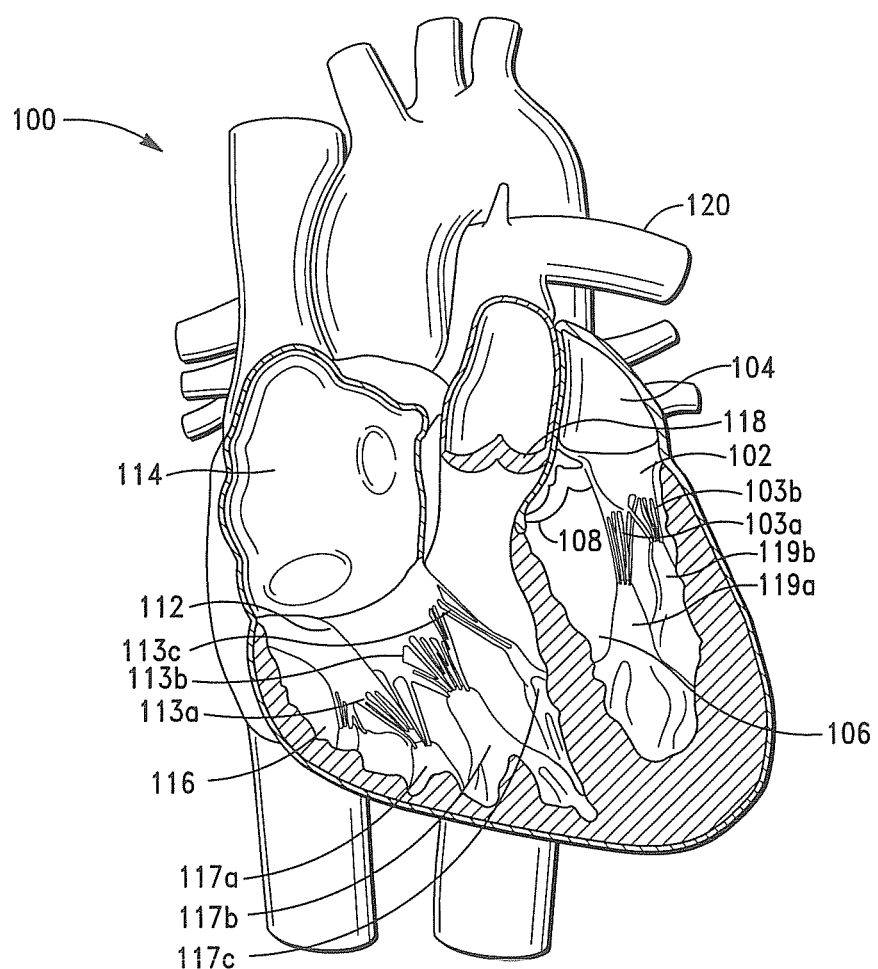

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The terms "extracellular matrix", "ECM", and "ECM material" are used interchangeably herein, and mean and include a collagen-rich substance that is found in between cells in mammalian tissue, and any material processed therefrom, e.g. decellularized ECM.

According to the invention, ECM can be derived from a variety of mammalian tissue sources and tissue derived therefrom, including, without limitation, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, tissue surrounding growing bone, placental tissue, omentum tissue, cardiac tissue, kidney tissue, pancreas tissue, lung tissue, and combinations thereof. The ECM material can also comprise collagen from mammalian sources.

The term "acellular ECM", as used herein, means and includes ECM that has a reduced content of cells, i.e. decellularized ECM.

The terms "urinary bladder submucosa (UBS)", "small intestine submucosa (SIS)" and "stomach submucosa (SS)" also mean and include any UBS and/or SIS and/or SS tissue that includes the tunica mucosa (which includes the transitional epithelial layer and the tunica propria), submucosal layer, one or more layers of muscularis, and adventitia (a loose connective tissue layer) associated therewith.

ECM can also be derived from basement membrane of mammalian organs/tissue, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

According to the invention, the ECM can be derived from xenogeneic and allogeneic tissue sources.

ECM can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussusceptive angiogenesis, sprouting angiogenesis, therapeutic angiogenesis and vasculogenesis.

The term "adverse inflammatory response", as used herein, means and includes a physiological response that is sufficient to induce constitutive clinically relevant expression of pro-inflammatory cytokines, such as interleukin-1 beta (IL-13) and monocyte chemoattractant protein-1 (MCP-1) in vivo.

The term "adverse biological response", as used herein, means and includes a physiological response that is sufficient to induce a biological process and/or restrict a phase associated with biological tissue healing in vivo, including without limitation, neovascularization and remodeling of the damaged biological tissue. The term "adverse biological response" thus includes an "adverse inflammatory response", e.g. development of fibrotic tissue.

The term "biologically active agent", as used herein, means and includes agent that induces or modulates a physiological or biological process, or cellular activity, e.g., induces proliferation, and/or growth and/or regeneration of tissue.

The term "biologically active agent" thus means and includes a growth factor, including, without limitation, fibroblast growth factor-2 (FGF-2), transforming growth factor beta (TGF-β), and vascular epithelial growth factor (VEGF).

The term "biologically active agent" also means and includes a cell, including, without limitation, human embryonic stem cells, myofibroblasts, mesenchymal stem cells, and hematopoietic stem cells.

The term "biologically active agent" also means and includes an exosome and/or microsome.

The terms "exosome" and "microsome" as used herein mean and include a lipid bilayer structure that contains or encapsulates a biologically active agent and/or pharmacological agent, including, without limitation, a growth factor, e.g. TGF-β, TGF-α, VEGF and insulin-like growth factor (IGF-I), a cytokine, e.g. interleukin-8 (IL-8), a transcription factor and micro RNA (miRNA).

The term "biologically active agent" also means and includes agents commonly referred to as a "protein", "peptide" and "polypeptide", including, without limitation, collagen (types I-V), proteoglycans and glycosaminoglycans (GAGs).

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent" and "drug" thus mean and include, without limitation, vancomycin and gentamicin.

The terms "pharmacological agent", "active agent" and "drug" also mean and include Class I-Class V antiarrhythmic agents.

The terms "pharmacological agent", "active agent", "drug" and "active agent formulation" further mean and include, without limitation, the following anti-fibrotics: paclitaxel, sirolimus and derivatives thereof, including everolimus.

The terms "pharmacological agent", "active agent" and "drug" also mean and include a statin, i.e. a HMG-CoA reductase inhibitor, including, without limitation, atorvastatin (Lipitor®), cerivastatin, fluvastatin (Lescol®), lovastatin (Mevacor®, Altocor®, Altoprev®), mevastatin, pitavastatin (Livalo®, Pitava), pravastatin (Pravachol®, Selektine®, Lipostat®), rosuvastatin (Crestor®), and simvastatin (Zocor®, Lipex®).

Additional biologically active and pharmacological agents are set forth in Co-pending priority U.S. application Ser. No. 15/206,833, which is expressly incorporated herein in its entirety.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to prosthetic tissue valves that can be readily employed to selectively replace diseased or defective valves in the heart, and methods for attaching (or anchoring) same to cardiovascular structures and/or tissue.

In some embodiments of the invention, the prosthetic tissue valves comprise continuous conical shaped sheet members.

In some embodiments of the invention, the prosthetic tissue valves comprise ribbon structures.

In some embodiments of the invention, the ribbon structures comprise a plurality of elongated ribbon members.

In a preferred embodiment of the invention, the edge regions of the ribbon members are positioned proximate each other and form a plurality of fluid flow modulating regions.

In a preferred embodiment, the distal ends of the ribbon members are in a joined relationship, wherein fluid flow through the joined distal ends of the ribbon members is restricted.

As indicated above, in some embodiments of the invention, the proximal ends of prosthetic tissue valves of the invention comprise an annular ring that is designed and configured to securely engage the prosthetic tissue valves to a valve annulus (and, hence, cardiovascular tissue associated therewith).

In some embodiments of the invention, the annular ring comprises at least one anchoring mechanism that is configured to position the prosthetic tissue valves proximate a valve annulus and maintain contact therewith for a predetermined anchor support time period. According to the invention, the anchoring mechanisms can comprise various forms and materials, such as disclosed in U.S. Pat. No. 9,044,319, which is incorporated by reference herein in its entirety.

In some embodiments of the invention, the anchoring mechanisms are configured to position ECM prosthetic tissue valves of the invention proximate a valve annulus and maintain contact therewith for a predetermined temporary anchor support period of time within the process of tissue regeneration.

In some embodiments of the invention, the distal end of the prosthetic tissue valves comprises a structural ring.

According to the invention, the prosthetic tissue valves and/or annular ring and/or structural ring can comprise various biocompatible materials and compositions formed therefrom.

In some embodiments of the invention, the prosthetic tissue valves and/or annular ring and/or structural ring comprise an ECM composition comprising acellular ECM derived from a mammalian tissue source.

According to the invention, the ECM can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety.

The mammalian tissue sources include, without limitation, the small intestine, large intestine, stomach, lung, liver, kidney, pancreas, peritoneum, placenta, heart, bladder, prostate, tissue surrounding growing enamel, tissue surrounding growing bone, and any fetal tissue from any mammalian organ.

The mammalian tissue can thus comprise, without limitation, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, placental tissue, omentum tissue, cardiac tissue, kidney tissue, pancreas tissue, lung tissue, and combinations thereof. The ECM can also comprise collagen from mammalian sources.

In some embodiments, the mammalian tissue source comprises an adolescent mammalian tissue source, e.g. tissue derived from a porcine mammal less than 3 years of age.

According to the invention, the ECM can also be derived from the same or different mammalian tissue sources, as disclosed in Co-Pending application Ser. Nos. 13/033,053 and 13/033,102; which are incorporated by reference herein.

In a preferred embodiment of the invention, the ECM comprises sterilized and decellularized (or acellular) ECM.

According to the invention, the ECM can be sterilized and decellularized by various conventional means.

In some embodiments of the invention, the ECM is sterilized and decellularized via applicant's proprietary process disclosed in Co-Pending U.S. application Ser. No. 13/480,205; which is expressly incorporated by reference herein in its entirety.

As indicated above, in some embodiments of the invention, the ECM composition (and, hence, prosthetic tissue valve and/or annular ring and/or structural ring formed therefrom) further comprises at least one additional biologically active agent or composition, i.e. an agent that induces or modulates a physiological or biological process, or cellular activity, e.g., induces proliferation, and/or growth and/or regeneration of tissue.

According to the invention, suitable biologically active agents include any of the aforementioned biologically active agents, including, without limitation, the aforementioned growth factors, cells and proteins.

Thus, in some embodiments of the invention, the biologically active agent comprises a growth factor, including, without limitation, transforming growth factor beta (TGF-β), fibroblast growth factor-2 (FGF-2), and vascular epithelial growth factor (VEGF).

In some embodiments of the invention, the biologically active agent comprises an exosome (referred to hereinafter as an "exosome augmented ECM composition").

As discussed in detail in Applicant's Co-pending U.S. application Ser. No. 15/386,640, exosomes significantly enhance the delivery of biologically active agents to cells through two seminal properties/capabilities.

The first property comprises the capacity of exosomes to shield the encapsulated biologically active agents (via the exosome lipid bilayer) from proteolytic agents, which can, and often will, degrade unshielded (or free) bioactive molecules and render the molecules non-functional in biological tissue environments.

The second property of exosomes comprises the capacity to directly and, hence, more efficiently deliver biologically active agents to endogenous cells in the biological tissue. As is well known in the art, endogenous cells typically do not comprise the capacity to "directly" interact with "free" biologically active agents, such as growth factors. There must be additional biological processes initiated by the endogenous cells to interact directly with biologically active agents, e.g. expression of receptor proteins for or corresponding to the biologically active agents.

As also set forth in Co-pending U.S. application Ser. No. 15/386,640, exosomes facilitate direct interaction by and between endogenous cells and exosome encapsulated biologically active agents (and, hence, direct delivery of bioactive molecules to endogenous cells), which enhances the bioactivity of the agents.

Thus, it is contemplated that, following placement of a prosthetic tissue valve comprising an exosome augmented ECM composition on or in a cardiovascular structure (or structures) of a subject, e.g. valve annulus, and, hence, damaged cardiovascular tissue associated therewith, the ECM prosthetic tissue valve will induce a multitude of significant biological processes in vivo, including significantly enhanced inflammation modulation of the cardiovascular tissue, and significantly induced neovascularization, stem cell proliferation, remodeling of the cardiovascular tissue, and regeneration of new tissue and tissue structures.

By way of example, when an exosome augmented ECM composition comprising encapsulated IL-8 (and, hence, tissue valve formed therefrom) is disposed proximate damaged cardiovascular tissue, the exosome augmented ECM composition and, hence, tissue valve formed therefrom modulates the transition of M1 type "acute inflammatory" macrophages to M2 type "wound healing" macrophages initiated by the acellular ECM.

By way of further example, when an exosome augmented ECM composition comprising encapsulated miRNAs (and, hence, tissue valve formed therefrom) is disposed proximate damaged cardiovascular tissue, the exosome augmented ECM composition and, hence, tissue valve formed therefrom induce enhanced stem cell proliferation via the delivery of exosome encapsulated miRNAs and transcription factors to the damaged cardiovascular tissue, which signals the endogenous stem cells to bind and/or attach to the acellular ECM and proliferate.

According to the invention, the exosomes can be processed and derived from a mammalian fluid composition, including, without limitation, blood, amniotic fluid, lymphatic fluid, interstitial fluid, pleural fluid, peritoneal fluid, pericardial fluid and cerebrospinal fluid.

The exosomes can also be derived and, hence, processed from in vitro or in vivo cultured cells, including, without limitation, one of the aforementioned cells, e.g., mesenchymal stem cells and hematopoietic stem cells.

The exosomes can also comprise semi-synthetically generated exosomes that are derived from an exosome producing cell line.

As also indicated above, in some embodiments of the invention, the ECM composition (and, hence, prosthetic tissue valve and/or annular ring and/or structural ring formed therefrom) further comprises at least one pharmacological agent or composition (or drug), i.e. an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned pharmacological agents and agents set forth in Applicant's Co-pending U.S. application Ser. No. 15/206,833.

It is thus contemplated that, in some embodiments of the invention, following placement of a prosthetic tissue valve comprising an ECM composition of the invention on or in a cardiovascular structure (or structures) of a subject, e.g. valve annulus, and, hence, damaged cardiovascular tissue associated therewith, the ECM tissue valve will become populated with cells from the subject that will gradually remodel the ECM into cardiovascular tissue and tissue (and, hence, valve) structures.

It is further contemplated that, following placement of a prosthetic tissue valve comprising an ECM composition of the invention on or in a cardiovascular structure (or structures) of a subject, and, hence, damaged cardiovascular tissue associated therewith, stem cells will migrate to the ECM tissue valve from the point(s) at which the valve is attached to the cardiovascular structure or structures.

It is still further contemplated that, during circulation of epithelial and endothelial progenitor cells after placement of an ECM tissue valve on a cardiovascular structure (or structures), the surfaces of an ECM tissue valve will rapidly become lined or covered with epithelial and/or endothelial progenitor cells.

As discussed in detail below, it is still further contemplated that, in some embodiments of the invention, following placement of an ECM prosthetic tissue valve of the invention on or in a cardiovascular structure (or structures) in a subject and, hence, cardiovascular tissue associated therewith, the ECM prosthetic tissue valve will induce "modulated healing" of the cardiovascular structure(s) and cardiovascular tissue associated therewith.

It is still further contemplated that the points at which an ECM tissue valve is attached to a cardiovascular structure (or structures) in a subject will serve as points of constraint that direct the remodeling of the ECM into cardiovascular tissue and valve structures that are identical or substantially identical to properly functioning native cardiovascular tissue and valve structures.

As indicated above, in some embodiments of the invention, the prosthetic tissue valves comprise a polymeric composition comprising a biodegradable polymeric material. According to the invention, suitable polymeric materials, include, without limitation, polyurethane urea, porous polyurethane urea (Artelon®), polypropylene, poly(ε-caprolactone) (PCL), poly(glycerol sebacate) (PGS) and polyethylene terephthalate (Dacron®).

According to the invention, in some embodiments of the invention, the annular ring and/or structural ring similarly comprise a polymeric composition comprising a biodegradable polymeric material. According to the invention, suitable biodegradable polymeric materials comprise, without limitation, polycaprolactone (PCL), porous polyurethane urea (Artelon®), polyglycolide (PGA), polylactide (PLA), poly (s-caprolactone) (PCL), poly dioxanone (a polyether-ester), poly lactide-co-glycolide, polyamide esters, polyalkalene esters, polyvinyl esters, polyvinyl alcohol, and polyanhydrides.

According to the invention, the polymeric composition can further comprise a natural polymer, including, without limitation, polysaccharides (e.g. starch and cellulose), proteins (e.g., gelatin, casein, silk, wool, etc.), and polyesters (e.g., polyhydroxyalkanoates).

The polymeric composition can also comprise a hydrogel composition, including, without limitation, polyurethane, poly(ethylene glycol), poly(propylene glycol), poly(vinylpyrrolidone), xanthan, methyl cellulose, carboxymethyl cellulose, alginate, hyaluronan, poly(acrylic acid), polyvinyl alcohol, acrylic acid, hydroxypropyl methyl cellulose, methacrylic acid, $\alpha\beta$-glycerophosphate, $\eta$-carrageenan, 2-acrylamido-2-methylpropanesulfonic acid, and $\beta$-hairpin peptide.

In some embodiments of the invention, the polymeric composition comprises poly(urethane urea); preferably, Artelon® distributed by Artimplant AB in Goteborg, Sweden.

In some embodiments, the polymeric composition comprises poly(glycerol sebacate) (PGS).

According to the invention, the polymeric composition can further comprise a non-biodegradable polymer, including, without limitation, polytetrafluoro ethylene (Teflon®) and polyethylene terephthalate (Dacron®).

In some embodiments of the invention, annular ring and/or structural ring comprise a biocompatible metal. According to the invention, suitable metals comprise, without limitation, Nitinol®, stainless steel and magnesium.

As indicated above, in some embodiments of the invention, it is contemplated that, following placement of an ECM prosthetic tissue valve of the invention on or in a cardiovascular structure (or structures) in a subject and, hence, cardiovascular tissue associated therewith, the ECM prosthetic tissue valve will induce "modulated healing" of the cardiovascular structure(s) and cardiovascular tissue associated therewith.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, the ECM prosthetic tissue valves of the invention are specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of an ECM prosthetic tissue valve of the invention to restrict the expression of inflammatory components. By way of example, according to the invention, when a prosthetic tissue valve (and/or annular ring and/or structural ring) of the invention comprises a statin augmented ECM composition, i.e. a composition comprising ECM and a statin, and the ECM prosthetic tissue valve is positioned proximate damaged biological tissue, e.g., attached to a valve annulus, the ECM prosthetic tissue valve restricts expression of monocyte chemoattractant protein-1 (MCP-1) and chemokine (C—C) motif ligand 2 (CCR2).

In some embodiments of the invention, "modulated healing" means and includes the ability of an ECM prosthetic tissue valve of the invention to alter a substantial inflammatory phase (e.g., platelet or fibrin deposition) at the beginning of the tissue healing process. As used herein, the phrase "alter a substantial inflammatory phase" refers to the ability of a prosthetic tissue valve of the invention to substantially reduce the inflammatory response at a damaged tissue site, e.g. valve annulus, when in contact with tissue at the site.

In such an instance, a minor amount of inflammation may ensue in response to tissue injury, but this level of inflammation response, e.g., platelet and/or fibrin deposition, is substantially reduced when compared to inflammation that takes place in the absence of an ECM prosthetic tissue valve of the invention.

The term "modulated healing" also refers to the ability of an ECM prosthetic tissue valve of the invention to induce host tissue proliferation, bioremodeling, including neovascularization, e.g., vasculogenesis, angiogenesis, and intussusception, and regeneration of new tissue and tissue structures with site-specific structural and functional properties, when disposed proximate damaged tissue, e.g. valve annulus.

Thus, in some embodiments of the invention, the term "modulated healing" means and includes the ability of an ECM prosthetic tissue valve of the invention to modulate inflammation and induce host tissue proliferation and remodeling, and regeneration of new tissue when disposed proximate damaged tissue.

It is further contemplated that, during a cardiac cycle after placement of an ECM prosthetic tissue valve on a valve structure or structures, wherein the ECM prosthetic tissue valve is subjected to physical stimuli, adaptive regeneration of the prosthetic tissue valve is also induced.

By the term "adaptive regeneration," it is meant to mean the process of inducing modulated healing of damaged tissue concomitantly with stress-induced hypertrophy of an ECM prosthetic tissue valve of the invention, wherein the ECM prosthetic tissue valve adaptively remodels and forms functioning valve structures that are substantially identical to native valve structures.

As indicated above, it is further contemplated that the points at which an ECM prosthetic tissue valve is attached to a cardiovascular structure (or structures) in a subject will serve as points of constraint that direct the remodeling of the ECM into cardiovascular tissue and valve structures that are substantially identical to properly functioning native cardiovascular tissue and valve structures.

Figure 2A:
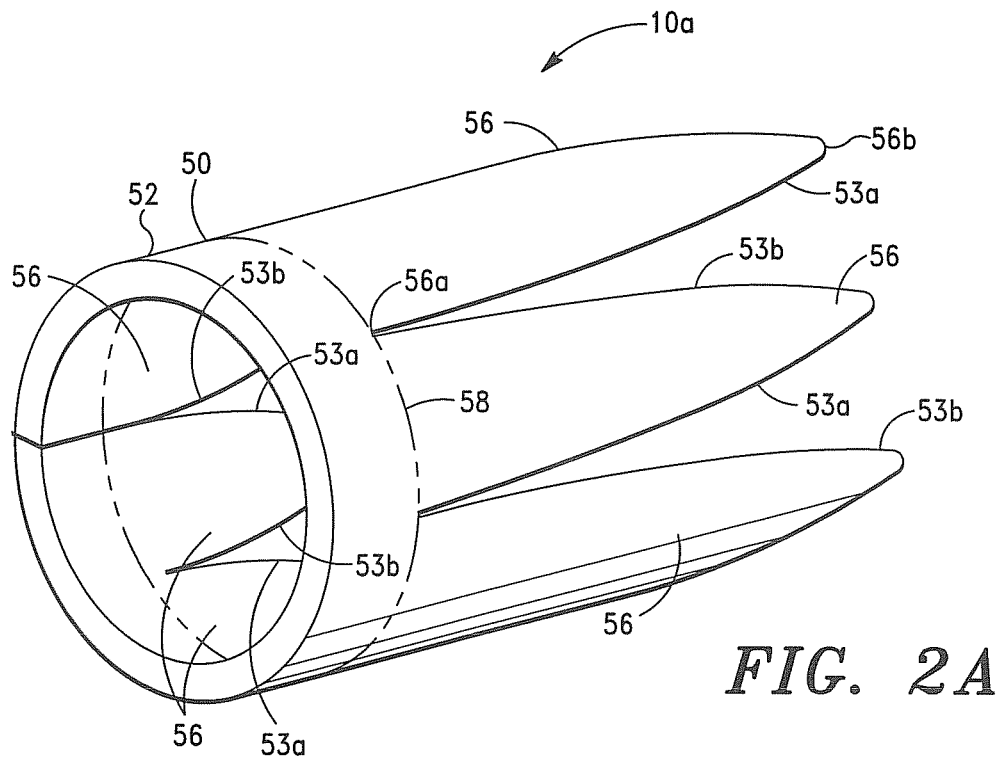
FIG. 2A is a perspective view of an embodiment of one prosthetic "ribbon structure" tissue valve, in accordance with the invention.
Figure 2B:
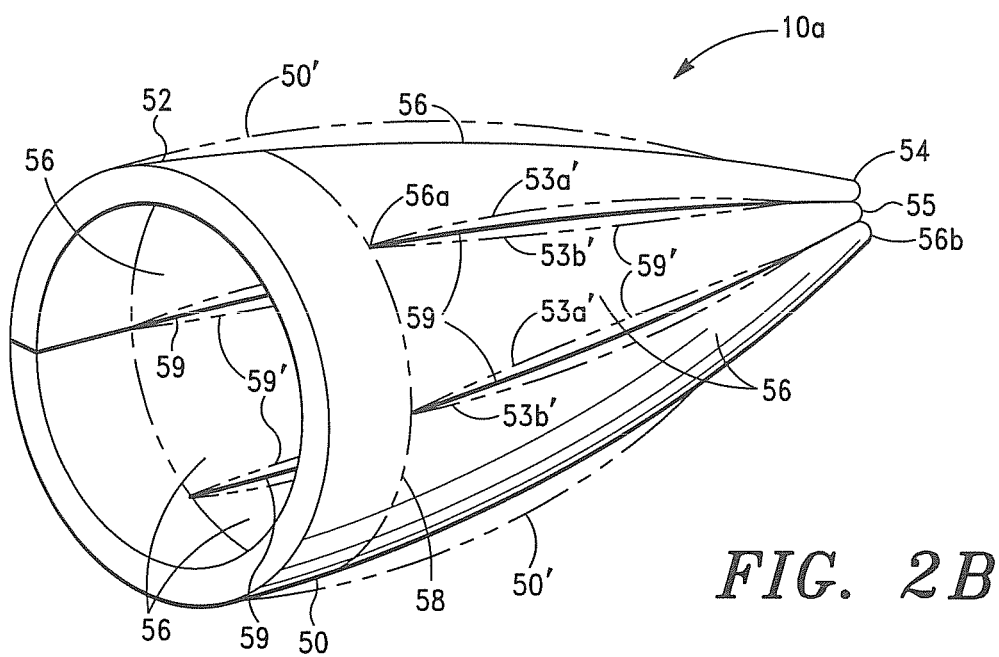
FIG. 2B is a perspective view of the tissue valve shown in FIG. 2A in an operational configuration, in accordance with the invention.

Referring now to FIGS. 2A and 2B, there is shown one embodiment of a prosthetic "ribbon structure" tissue valve of the invention, where FIG. 2A illustrates the prosthetic tissue valve, denoted 10a, in a pre-deployment configuration and FIG. 2B illustrates the prosthetic tissue valve 10a in a deployed operational configuration.

As illustrated in FIGS. 2A and 2B, in a preferred embodiment of the invention, the prosthetic tissue valve 10a comprises a base member 50 comprising a proximal valve annulus engagement end 52 having a circumferential ribbon connection region 58, and a distal end 54. The base member 50 further comprises a plurality of ribbon members or ribbons 56 that are connected to and extend from the ribbon connection region 58.

As further illustrated in FIGS. 2A and 2B, each of the plurality of ribbons 56 comprise proximal and distal ends 56a, 56b, and first and second edge regions 53a, 53b that extend from the circumferential ribbon connection region 58 to the distal ends 56b of each of the ribbons 56 and, hence, distal end 54 of the base member 50.

In a preferred embodiment, the base member 50 similarly comprises an ECM composition comprising acellular ECM derived from one of the aforementioned mammalian tissue sources.

As illustrated in FIG. 2B, in some embodiments, the ribbons 56 of the formed valve 10a taper to a substantially coincident point 55, wherein the base member 50 has a substantially conical shape.

In a preferred embodiment, the distal ends 56b of the ribbons 56 are in a joined relationship, wherein fluid flow through the joined distal ends 56b of the ribbons 56 is restricted.

As further illustrated in FIG. 2B, the proximal ends 56a of ribbons 56 are positioned circumferentially about the circumferential ribbon connection region 58 of the base member 50, wherein the first edge regions 53a and the second edge regions 53b of the ribbons 56 are positioned adjacent each other and form a plurality of fluid flow modulating regions 59.

In a preferred embodiment of the invention, the base member 50 is configured to expand during positive fluid flow through the base member 50, as shown in phantom and denoted 50', and contract during negative fluid flow through the base member 50, e.g. regurgitating blood flow.

In a preferred embodiment, the fluid flow modulating regions 59 are configured to open during expansion of the base member 50' (as shown in phantom and denoted 59'), i.e. the first and second edge regions 53a, 53b separate, as shown in phantom and denoted 53a', 53b', wherein the positive fluid flow is allowed to be transmitted through the fluid flow modulating regions 59', and close during the contraction of the base member 50, wherein the negative fluid flow through base member 50 is restricted, more preferably, abated.

According to the invention, the base member 50 can comprise any number of ribbons 56. In some embodiments of the invention, the base member 50 has four (4) equally spaced ribbons 56.

According to the invention, the proximal end of the prosthetic tissue valves of the invention preferably comprise a circumference, i.e. operative valve circumference, in the range of approximately 20 mm to 220 mm.

According to the invention, the prosthetic tissue valves of the invention can also comprise any length. In some embodiments of the invention, the prosthetic tissue valves 10f have a length in the range of approximately 10 mm to 100 mm.

Figure 2C:
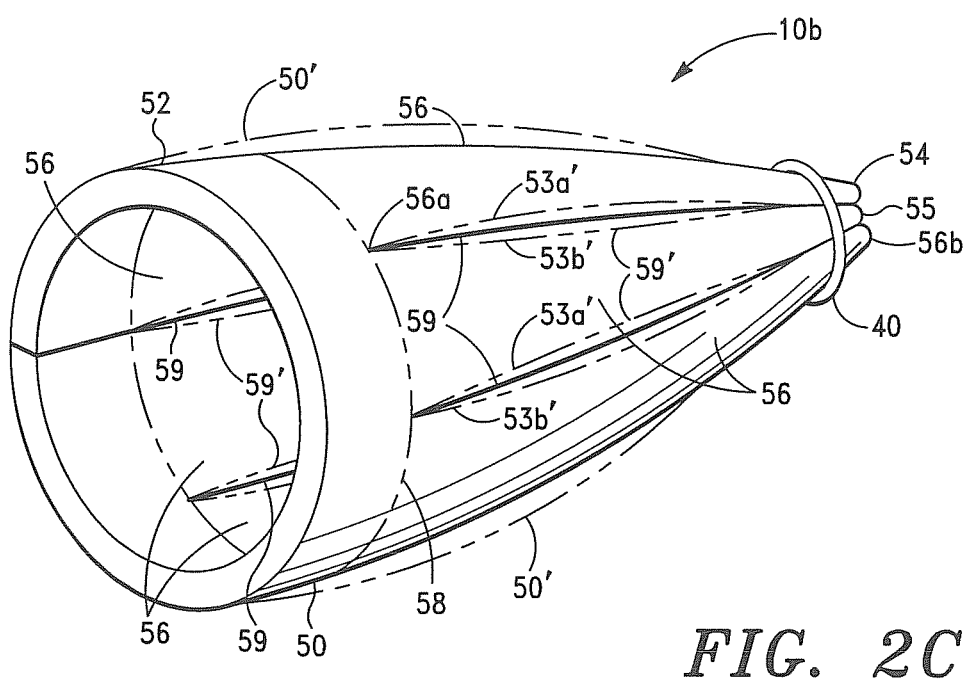
FIG. 2C is a perspective partial sectional view of another embodiment of the tissue valve shown in FIG. 2B having a structural ring disposed at the distal end of the valve, in accordance with the invention.

Referring now to FIG. 2C, there is shown another embodiment of the prosthetic tissue valve 10a that is shown in FIGS. 2A and 2B. As illustrated in FIG. 2C, the prosthetic tissue valve, now denoted 10b, includes a support ring 40 that is disposed on the distal end 54 of the valve 10b.

According to the invention, the structural ring 40 is preferably sized and configured to receive ribbons 56 therein in close proximity to each other, as shown in FIG. 2C.

Figure 3A:
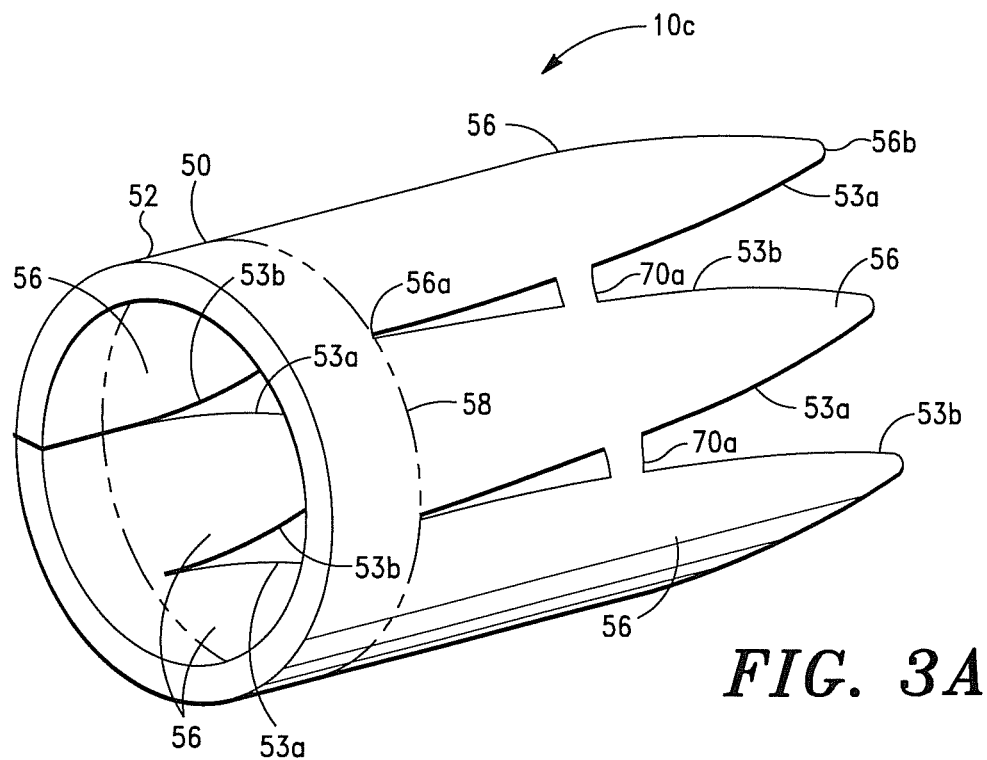
FIG. 3A is a perspective view of one embodiment of a prosthetic "ribbon structure" tissue valve having an integral ribbon coupling member, in accordance with the invention.
Figure 3B:
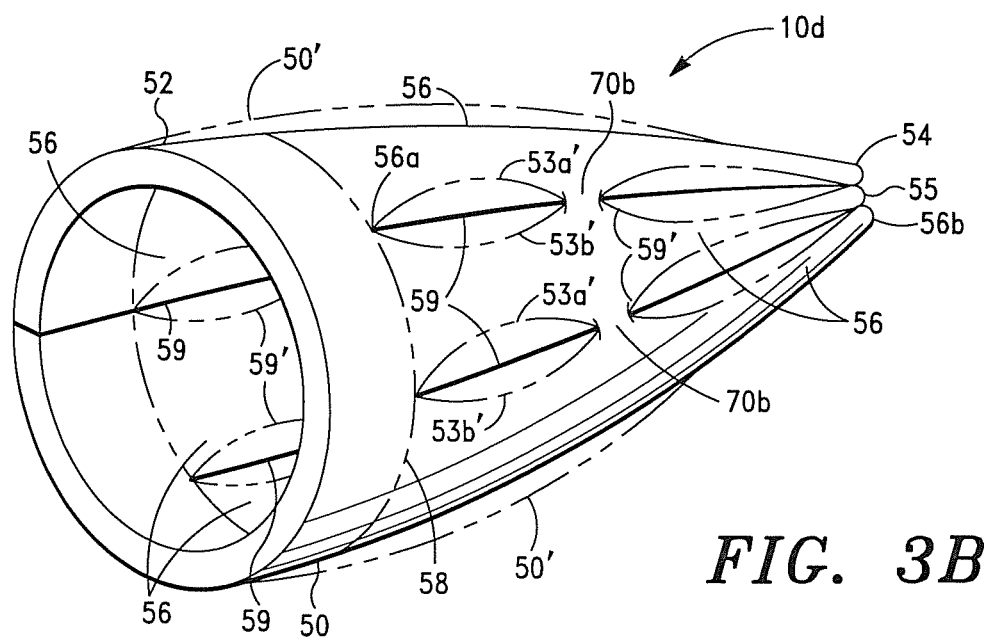
FIG. 3B is a perspective view of the tissue valve shown in FIG. 3A in an operational configuration, in accordance with the invention.

Referring now to FIGS. 3A and 3B there are shown further embodiments of prosthetic "ribbon structure" tissue valves (denoted "10c" and "10d"). As illustrated in FIGS. 3A and 3B, the tissue valves 10c, 10d also comprise a base member 50 comprising a proximal valve annulus engagement end 52 having a circumferential ribbon connection region 58, and a distal end 54. The base member 50 further comprises a plurality of ribbon members or ribbons 56 that are connected to and extend from the ribbon connection region 58.

As further illustrated in FIGS. 3A and 3B, in a preferred embodiment, the tissue valves 10c, 10d further comprise at least one constraining band or coupling member (denoted "70a" in FIG. 3A and "70b" in FIG. 3B). According to the invention, the coupling member is sized and configured to couple (or join) a ribbon 56 to adjacent ribbons, i.e. couple a first edge region 53a of a first ribbon 56 to the second edge region 53b of a second ribbon 56, at a predetermined region.

More preferably, the tissue valves 10c, 10d comprise a plurality of coupling members that are sized and configured to couple (or join) each ribbon 56 to adjacent ribbons at a predetermined region.

According to the invention, the coupling members 70a, 70b can be disposed at any region between the proximal and distal ends 56a, 56b of the ribbons 56.

The coupling members 70a, 70b can also comprise any length.

According to the invention, the coupling members 70a, 70b can comprise separate or integral members. The coupling members 70a, 70b can also comprise a combination of separate and integral members.

According to the invention, the separate coupling members (not shown) can be attached to the ribbons via conventional means, e.g., suturing or an adhesive composition.

According to the invention, suitable adhesive compositions include, without limitation, poly(glycerol sebacate) (PGS), poly(glycerol sebacate) acrylate (PGSA) and collagen-based compositions.

According to the invention, the adhesive compositions can be crosslinked and/or cured via the combination of a photoinitiator and radiation.

In a preferred embodiment, the coupling members 70a, 70b comprise integral members, such as illustrated in FIGS. 3A and 3B, wherein a continuous prosthetic valve structure is provided.

In some embodiments of the invention, not shown, the coupling members 70a, 70b are sized and configured to intersect or cross each other.

Figure 3C:
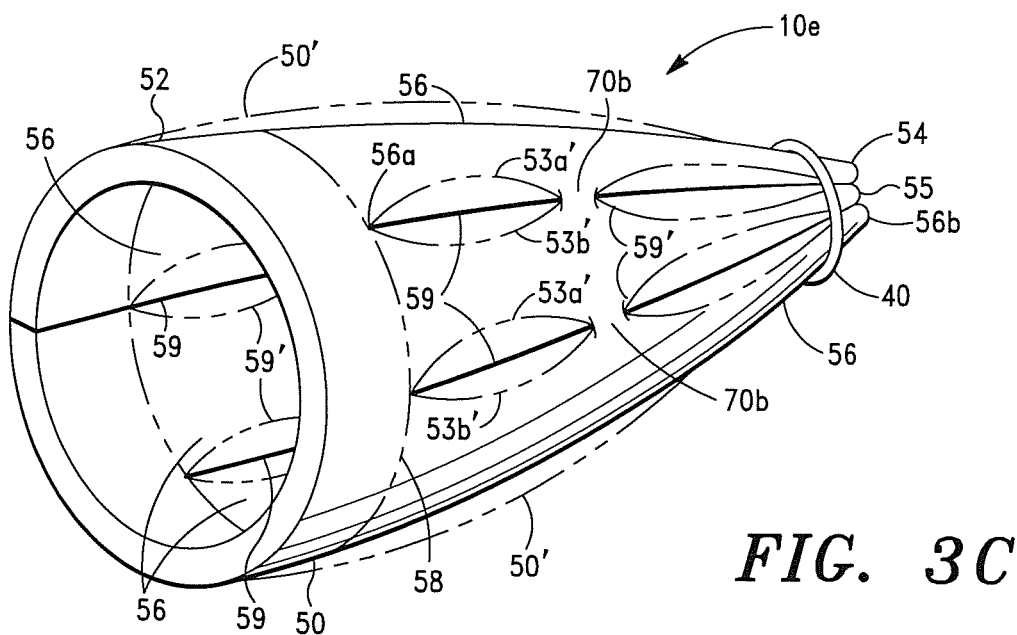
FIG. 3C is a perspective view of another embodiment the tissue valve shown in FIG. 3B having a support ring disposed at the distal end of the valve, in accordance with the invention.

Referring now to FIG. 3C, there is shown another embodiment of the prosthetic tissue valve 10d that is shown in FIG. 3B. As illustrated in FIG. 3C, the prosthetic tissue valve, now denoted 10e, similarly comprises a structural ring 40 that is disposed on the distal end 54 of the valve 10e.

In some embodiments of the invention, the prosthetic tissue valves 10d and 10e further comprise a supplemental support structure, such as described in Applicant's Co-pending U.S. application Ser. No. 15/206,871.

Figure 4:
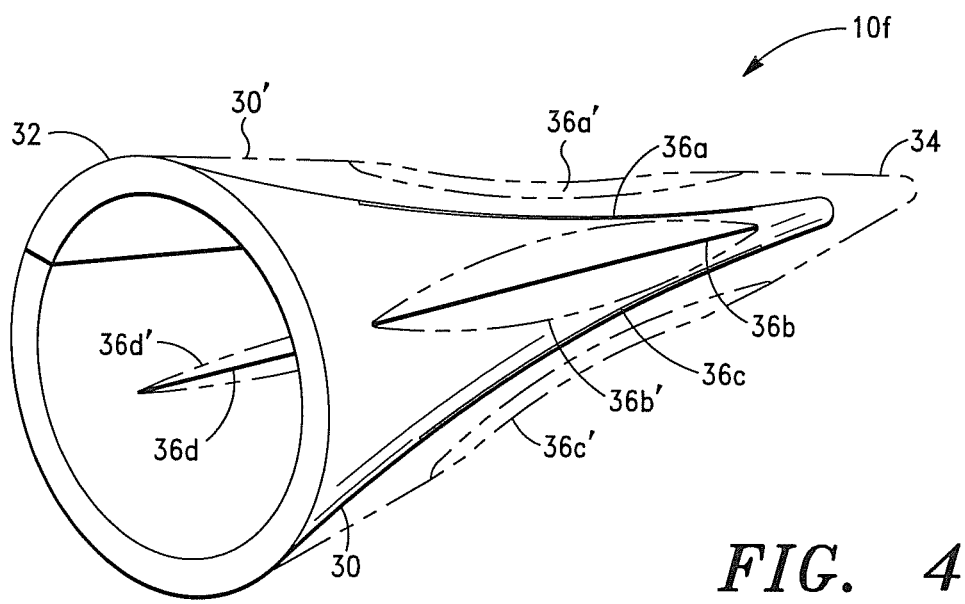
FIG. 4 is a perspective view of one embodiment of a prosthetic "sheet member" tissue valve, in accordance with the invention.

Referring now to FIG. 4, there is shown another embodiment of a prosthetic tissue valve of the invention (denoted "10f"). As illustrated in FIG. 4, the tissue valve 10f comprises a continuous conical shaped sheet member 30.

In a preferred embodiment, the sheet member 30 similarly comprises an ECM composition comprising acellular ECM derived from one of the aforementioned mammalian tissue sources, including, without limitation, small intestine submucosa (SIS), urinary bladder submucosa (UBS), mesothelial tissue, placental tissue and cardiac tissue.

As illustrated in FIG. 4, the tissue valve 10f further comprises proximal and distal ends 32, 34, and a plurality of open regions or interstices 36a-36d that are preferably disposed linearly over a portion of the length of the sheet member 30.

As discussed in detail in Co-pending U.S. application Ser. No. 15/206,833, the sheet member 30 is preferably configured to expand during positive fluid flow through the sheet member 30, as shown in phantom and denoted 30', and contract during negative fluid flow through the sheet member 30, e.g. regurgitating blood flow.

The interstices 36a-36d are also preferably configured to open during the noted expansion of the conical shaped member 30' (denoted 36a', 36b', 36c' and 36d'), wherein the positive fluid flow is allowed to be transmitted through the interstices 36a', 36b', 36c', 36d', and close during the noted contraction of the sheet member 30, wherein the negative fluid flow through said member 30 is restricted, more preferably, abated.

Figure 5:
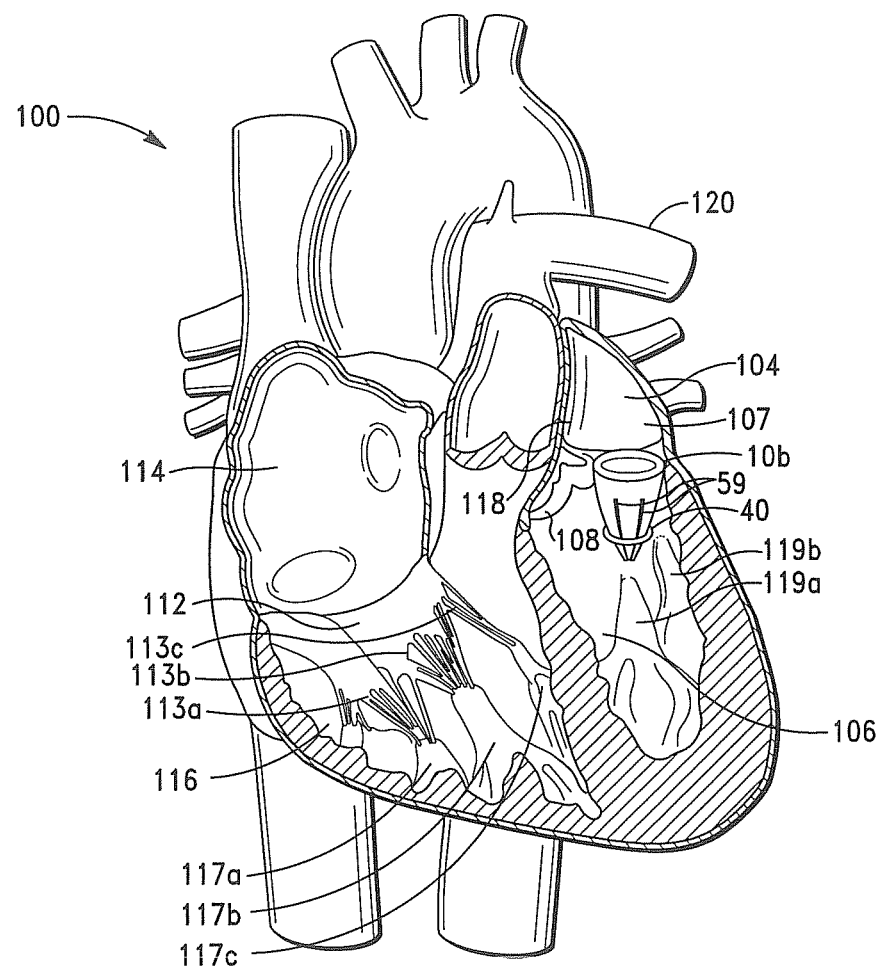
FIG. 5 is an illustration of the tissue valve shown in FIG. 2C secured to the mitral valve annulus region, in accordance with the invention.
Figure 6:
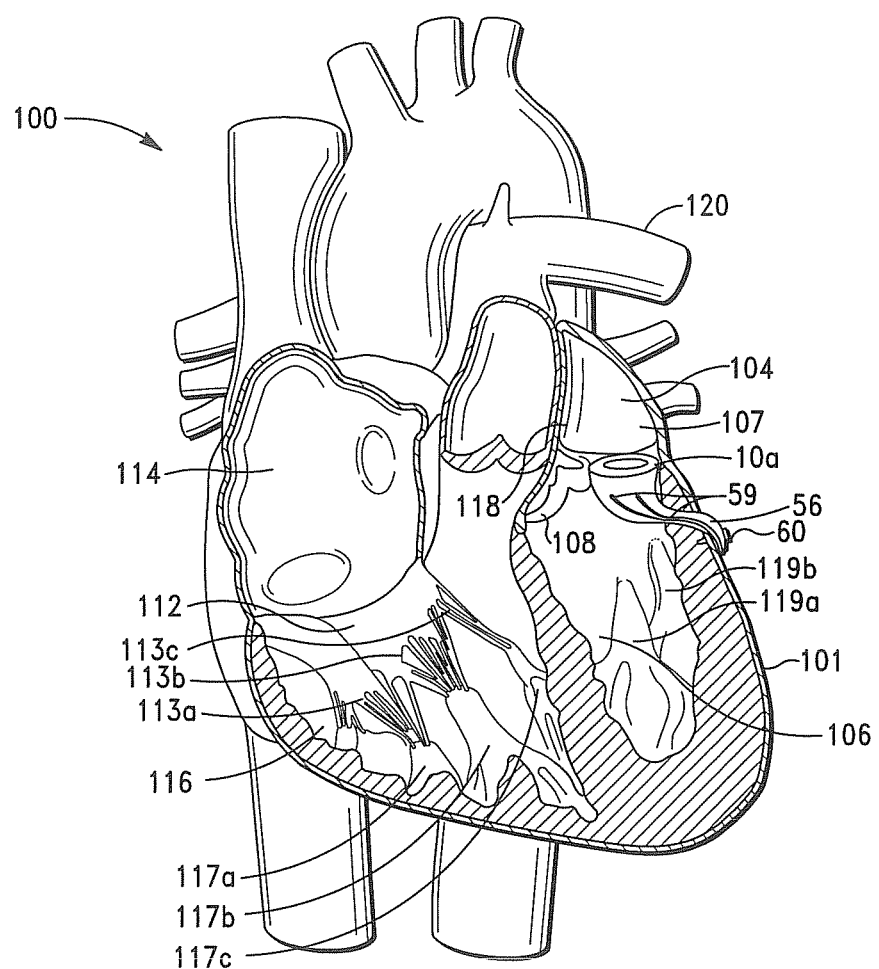
FIG. 6 is an illustration of the tissue valve shown in FIG. 2B secured to the mitral valve annulus region, in accordance with the invention.

Referring now to FIGS. 5 and 6, there are shown tissue valve 10b and 10a, respectively, disposed in mitral valve regions of a subject. Placement of the valves 10b and 10a in the mitral valve regions is described in detail in Applicant's Co-pending U.S. application Ser. No. 15/206,833.

As indicated above, it is contemplated that, when the prosthetic tissue valves of the invention comprise an ECM composition comprising acellular ECM (i.e. ECM prosthetic tissue valves), upon placement of the ECM prosthetic tissue valves to a valve structure, e.g., valve annulus 105, modulated healing of the valve structure and connecting cardiovascular structure tissue will be effectuated.

It is further contemplated that, following placement of the ECM prosthetic tissue valve of the invention on or in a cardiovascular structure (or structures) of a subject, the ECM prosthetic tissue valves will become populated with cells from the subject that will gradually remodel the ECM into cardiovascular tissue and tissue (and, hence, valve) structures.

It is further contemplated that, following placement of the ECM prosthetic tissue valves of the invention on a cardiovascular structure (or structures) in a subject, stem cells will migrate to the ECM prosthetic tissue valves from the point(s) at which the valves are attached to the cardiovascular structure, e.g., valve annulus, or structures, e.g., valve annulus and heart wall.

It is still further contemplated that the points at which the ECM prosthetic tissue valves of the invention are attached to a cardiovascular structure (or structures) in a subject will serve as points of constraint that direct the remodeling of the ECM into cardiovascular tissue and valve structures that are identical or substantially identical to properly functioning native cardiovascular tissue and valve structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic valve for modulating fluid flow through a cardiovascular structure during cardiac cycles of a heart, said fluid flow exhibiting a plurality of positive and negative flow pressures during said cardiac cycles, said prosthetic valve comprising:

a base valve structure comprising an extracellular matrix (ECM) composition, said ECM composition comprising acellular ECM from a mammalian tissue source, said base valve structure further comprising an open proximal valve annulus engagement end, a distal end, and a plurality of elongated ribbon members, said proximal valve annulus engagement end being configured to engage a valve annulus region of said cardiovascular structure, said proximal valve annulus engagement end, when engaged to said valve annulus region of said cardiovascular structure, being further configured and adapted to receive said fluid flow therein and direct said fluid flow into said base valve structure, said proximal valve annulus engagement end comprising a circumferential ribbon member connection region, each of said plurality of elongated ribbon members comprising a proximal end, a distal end, and a mid-ribbon member region disposed between said proximal and distal ends of said plurality of elongated ribbon members, said proximal ends of said plurality of elongated ribbon members being connected to said circumferential ribbon member connection region, whereby said plurality of elongated ribbon members project from said proximal valve annulus engagement end to said base valve structure distal end, each of said plurality of elongated ribbon members further comprising a first edge region that extends from said proximal end of each of said plurality of elongated ribbon members to said distal end of each of said plurality of elongated ribbon members and a second edge region that extends from said proximal end of each of said plurality of elongated ribbon members to said distal end of each of said plurality of elongated ribbon members, said plurality of elongated ribbon members being positioned circumferentially about said circumferential ribbon member connection region, wherein said first edge regions of said plurality of elongated ribbon members are positioned proximate said second edge regions of said plurality of elongated ribbon members and a plurality of fluid flow modulating regions is formed between adjacent elongated ribbon members of said plurality of elongated ribbon members, said distal ends of said plurality of elongated ribbon members being engaged to each other in a joined relationship at said base valve structure distal end, wherein said fluid flow through said distal end of said base valve structure is restricted during said fluid flow into said base valve structure while said fluid flow is allowed to be transmitted through at least one of said fluid flow modulating regions when said at least one of said fluid flow modulating regions is in an open position, said base valve structure further comprising at least one coupling member that connects said first edge region of a first elongated ribbon member of said plurality of elongated ribbon members to said second edge region of an adjacent second elongated ribbon member of said plurality of elongated ribbon members, said at least one coupling member being connected to said mid-ribbon member regions of said first elongated ribbon member and said adjacent second elongated ribbon member of said plurality of elongated ribbon members, whereby, said first elongated ribbon member and said adjacent second elongated ribbon member of said plurality of elongated ribbon members are coupled together, said base valve structure, when engaged to said valve annulus region of said cardiovascular structure and receives said fluid flow therein, being configured to transition from a pre-expanded position to an expanded position when said fluid flow exhibits a first positive flow pressure of said plurality of positive flow pressures, each of said plurality of fluid flow modulating regions being configured to transition from a closed position when said base valve structure is in said pre-expanded position, wherein each of said plurality of fluid flow modulating regions and said distal end of said base valve structure restricts said fluid flow through said base valve structure, to said open position when said base valve structure transitions to said expanded position, wherein each of said plurality of fluid flow modulating regions allows said fluid flow to be transmitted through said plurality of fluid flow modulating regions while said distal end of said base valve structure restricts said fluid flow through said distal end of said base valve structure, said base valve structure being further adapted to remodel into cardiovascular tissue and native valve structures and induce remodeling of damaged cardiovascular tissue and regeneration of new cardiovascular tissue when said proximal valve annulus engagement end of said base valve structure is engaged to said valve annulus region of said cardiovascular structure.

2. The prosthetic valve of claim 1, wherein said mammalian tissue source is selected from the group consisting of small intestine submucosa (SIS), urinary bladder submucosa (UBS), urinary basement membrane (UBM), liver basement membrane (LBM), stomach submucosa (SS), mesothelial tissue, placental tissue, omentum tissue, heart tissue and lung tissue.

3. The prosthetic valve of claim 1, wherein said ECM composition further comprises at least one exogenously added biologically active agent.

4. The prosthetic valve of claim 3, wherein said biologically active agent comprises a cell selected from the group consisting of a human embryonic stem cell, fetal cardiomyocyte, myofibroblast, and mesenchymal stem cell.

5. The prosthetic valve of claim 3, wherein said biologically active agent comprises a growth factor selected from the group consisting of transforming growth factor-beta (TGF-β), fibroblast growth factor-2 (FGF-2), and vascular epithelial growth factor (VEGF).

* * * * *